(12) United States Patent
Obabkov

(10) Patent No.: US 6,650,933 B1
(45) Date of Patent: Nov. 18, 2003

(54) METHOD FOR THE EXPRESS DIAGNOSIS OF THE PHYSIOLOGICAL CONDITION OF A BIOLOGICAL OBJECT AND DEVICE FOR REALIZING THE SAME

(76) Inventor: Anatoly Ivanovich Obabkov, kv. 36, d.40, ul. Cherdynskaya, g. Perm (RU), 614088

(*) Notice: Subject to any disclaimer, the term of this patent is extended or adjusted under 35 U.S.C. 154(b) by 0 days.

(21) Appl. No.: 10/019,361
(22) PCT Filed: Apr. 7, 2000
(86) PCT No.: PCT/RU00/00123
§ 371 (c)(1),
(2), (4) Date: Oct. 25, 2001
(87) PCT Pub. No.: WO00/65991
PCT Pub. Date: Nov. 9, 2000

(30) Foreign Application Priority Data

Apr. 28, 1999 (RU) .............................. 99108801

(51) Int. Cl.$^7$ ................................................ A61B 5/05
(52) U.S. Cl. ........................................................ 600/547
(58) Field of Search ............................ 600/547, 300, 600/549, 551, 573; 436/65, 164, 166

(56) References Cited

U.S. PATENT DOCUMENTS

| 3,949,736 A | 4/1976 | Vrana et al. |
| 4,832,034 A | 5/1989 | Pizziconi et al. |

FOREIGN PATENT DOCUMENTS

| SU | 1387980 | 4/1988 |
| SU | 1530171 | 12/1989 |

Primary Examiner—Max F. Hindenburg
Assistant Examiner—Brian Szmal
(74) Attorney, Agent, or Firm—Dellett & Walters

(57) ABSTRACT

The present invention relates to a method that involves collecting a sample of biological liquid, placing the same in a cell (1) for analysis, supplying a current through the cell from a frequency- and amplitude-adjustable generator (2) and measuring the conductivity Y1. The method also involves using a biological-liquid reference (12) through which a current is supplied at the same amplitude and frequency before measuring its conductivity Yr. The method further involves calculating a value $N_1=Y1/Yr$ and the biological object is in a normal condition when $N_1<1$, whereas a potential disease is diagnosed when $N_1>1$. The device of the present invention comprises an analysis cell (1) having a generator (2) connected thereto and also includes a differential amplifier (3), a detector (4) and a measuring unit (5) connected in series. The differential amplifier (3) includes first and second current summing inputs (6, 7) and the generator (2) is connected to the first summing input (6) of said differential amplifier (3). An amplifier (8) is also n provided and has first and second current summing inputs (9, 10), while an electrode (13) is connected to the second summing input (7) of the differential amplifier (3) and is capable of three-dimensional displacement so as to be brought into contact with the biological liquid in the analysis cell (1) and with the reference (12). The detector (4) is connected to the measuring unit (5) through the first summing input (9) of the added amplifier (8), while a voltage regulator (11) is connected thereto through the second summing input (10) of said amplifier (8).

11 Claims, 1 Drawing Sheet

US 6,650,933 B1

METHOD FOR THE EXPRESS DIAGNOSIS OF THE PHYSIOLOGICAL CONDITION OF A BIOLOGICAL OBJECT AND DEVICE FOR REALIZING THE SAME

FIELD OF INVENTION

This invention relates to medicine and may be used as medical equipment for integral assessment of the condition of a human being or an animal

BACKGROUND OF THE INVENTION

Known in the art are methods for diagnosis of the physiological condition of a biological object, which include collecting a sample of a biological fluid from a biological object and placing it in a cell for analysis, passing an electrical current from a frequency and amplitude modulated generator through the cell containing the biological fluid, measuring the impedance Y1 of the biological fluid sample, assessing the physiological condition of the biological object under the sample conductivity (U.S. Pat. No. 3,949,736; U.S. Pat. No. 4,038,975).

An advantage of the said method is that the impedance is measured with a frequency and amplitude modulated generator, which raises its descriptiveness.

A drawback of the said method is that the impedance is measured by a potential method, i.e., by registering voltages at a resistor dividing circuit, which impairs the measurement accuracy. When measuring impedances of biological fluids, the measurement accuracy is also significantly influenced by the ambient conditions, such as the ambient temperature, humidity, etc. The method provides for direct measurements of the impedance values of a biological medium without any regard to these factors. Moreover, a cell with a relatively large electrode area is used in the said method. Taking into account the fact that the measured biological medium has air inclusions, the stationary construction of the terminals and the cell does not allow to conduct accurate measurements for a long time interval, since in the course of time the terminals are covered with an oxide film and the cell accumulates the residues of the biological medium. The method does not provide for express (within a very short time) diagnosis of the physiological condition of a biological object by comparing the data on the impedance of a sample with the reference data that is also changed under the influence of the ambient atmosphere.

Also known in the art is a device for diagnosis of the physiological condition of a biological object, which comprises a cell for placing a biological fluid therein, a generator connected to the analysis cell and a differential amplifier and a measuring means connected in series, the said analysis cell is made with the possibility of being connected to the said differential amplifier (U.S. Pat. No. 1,387,980).

The said device also comprises a thermistor arranged in the cell, a current-to-voltage converter, a temperature compensator, a limiting amplifier, an analog-digital converter.

An advantage of the said device is the improved measurement accuracy owing to the monitoring and compensation of temperature-related factors.

The limitations of that technical solution are as follows: the device may be operated only at a fixed frequency and a fixed voltage of the generator, since the cell is included into the feedback loop of the amplifier, which leads to unstable operation of the circuit when the amplitude or the frequency of the generator is changed; the differential amplifier is connected to the voltage terminals of the cell, which additionally impairs accuracy and contributes to unstable operation of the circuit at the selected operation mode of the device—subtraction of voltages; the construction of the cell and the circuit is complicated due to the use of a thermistor and a current-to-voltage converter, a temperature compensator and an analog-digital converter; all the limitations due to the use of a stationary cell and the terminals are preserved, such as time-depended conductance of the terminals and the shell of the cell.

SUMMARY OF THE INVENTION

It is the primary object of this invention to provide a method for diagnosis of the physiological condition of a biological object, according to which a sample is collected and a biological fluid is analyzed so as to improve the functional capabilities, raise the accuracy and objectivity of measurements with due regard to the influence of the ambient atmosphere and that of errors of measuring means to the analysis data, as well a create a device for diagnosis of the physiological condition of a biological object, wherein a generator, a differential amplifier and other technical means are made and interconnected so as to enlarge the inventory of measuring means, raise the accuracy and expand the range of measurements, improve the convenience of operation and simplify the whole construction and, thus, to raise the quality and accuracy of measurements.

According to this invention, this object is achieved by improving the known method of diagnosis of the physiological condition of a biological object that involves collecting a sample of a biological fluid from the biological object, placing the sample in an analysis cell, passing a current supplied by a frequency and amplitude modulated generator through the analysis cell containing the biological fluid, and measuring the conductivity Y1 of the biological fluid sample, which conductivity is served to assess the physiological condition of the biological object, such improvement consists in that a biological fluid sample is collected from a biological object after leaving the quiescent state and awakening, a reference biological fluid is additionally used, a current of the same frequency and amplitude is passed through the reference biological fluid and its conductivity $Y_R$ is measured at constant temperatures of the reference and the analysis cell containing the biological fluid, the conductivity values Y1 and $Y_R$ are compared by determining the ratio $N_1 = Y1/Y_R$, where $N_1$ lower than 1 evidences the normal condition of the biological object and $N_1$ greater than 1 attests to a disorder in the physiological condition of the biological object.

Some other embodiments of the method are possible wherein:

- as the reference biological fluid a sample collected from a reference biological object is used, which is placed in the reference cell similar as to its electrical parameters to the analysis cell; and the conductivity $Y_R$ of the biological fluid sample contained in the reference cell is measured;
- as the biological fluid reference a resistor is used that has the conductivity equal to that of the biological fluid and the analysis cell;
- a second sample is collected from the biological object in the wake time before the first meal and is placed in an additional analysis cell similar as to its electrical parameters to the said analysis cell, the conductivity Y2 of the second sample is measured, the ratio $N_2 = Y2/Y_R$ is determined by the biological fluid conductivity in the additional analysis cell (18) and that in the reference cell, and the condition of the immune system is assessed by the compliance with the relation $N_1/N_2>1$, where at the value $N_1<1$ the immune system activity grows, but if $N_1$ approaches to 1 it is reduced;

saliva is used as the biological fluid;

urea is used as the biological fluid;

blood is used as the biological fluid.

The object of this invention is also attained owing to that the known device for the diagnosis of the physiological condition of a biological object contains the analysis cell intended for placing a biological fluid therein, a generator connected to the analysis cell and a differential amplifier, a detector and a measuring unit connected in series, the said analysis cell being made with the possibility of being connected to the differential amplifier; according to the invention, the differential amplifier is made with first and second current summing inputs, the generator is connected to the first summing input of the differential amplifier, additionally introduced are an amplifier having the first and the second summing inputs, a voltage regulator, a reference cell intended for placing a reference biological fluid into it, an electrode connected to the second summing input and made with the possibility of its spatial displacement for making contact with the biological fluid in the analysis cell and the reference cell, the detector being connected to the measuring unit through the first summing input of the amplifier and the voltage regulator being connected thereto through the second summing input of the amplifier.

Some other embodiments of the invention are possible, where:

an equivalent of the electrode is introduced that is made in the form of a resistor with the conductivity equal to that of the terminal and connected to the second summing input of the differential amplifier through a switch;

the generator is made as the output signal frequency and amplitude modulated unit;

the electrode is made as a coaxial probe with the cone-shaped tip.

Owing to the introduction of the reference cell, comparison of the characteristics of the biological fluid to the reference biological fluid as well as due to making the device in accordance with the above-said construction features having functional links therebetween, the object of the invention has been attained.

The said advantages as well as the features of this invention are explained by its best embodiment with references to the appended Figures. Since the method is realized while the device is operated, the description of the method, as the subject of the invention, is given in the section where the operation of the device is described.

DESCRIPTION OF THE BEST EMBODIMENT

Figure 1:
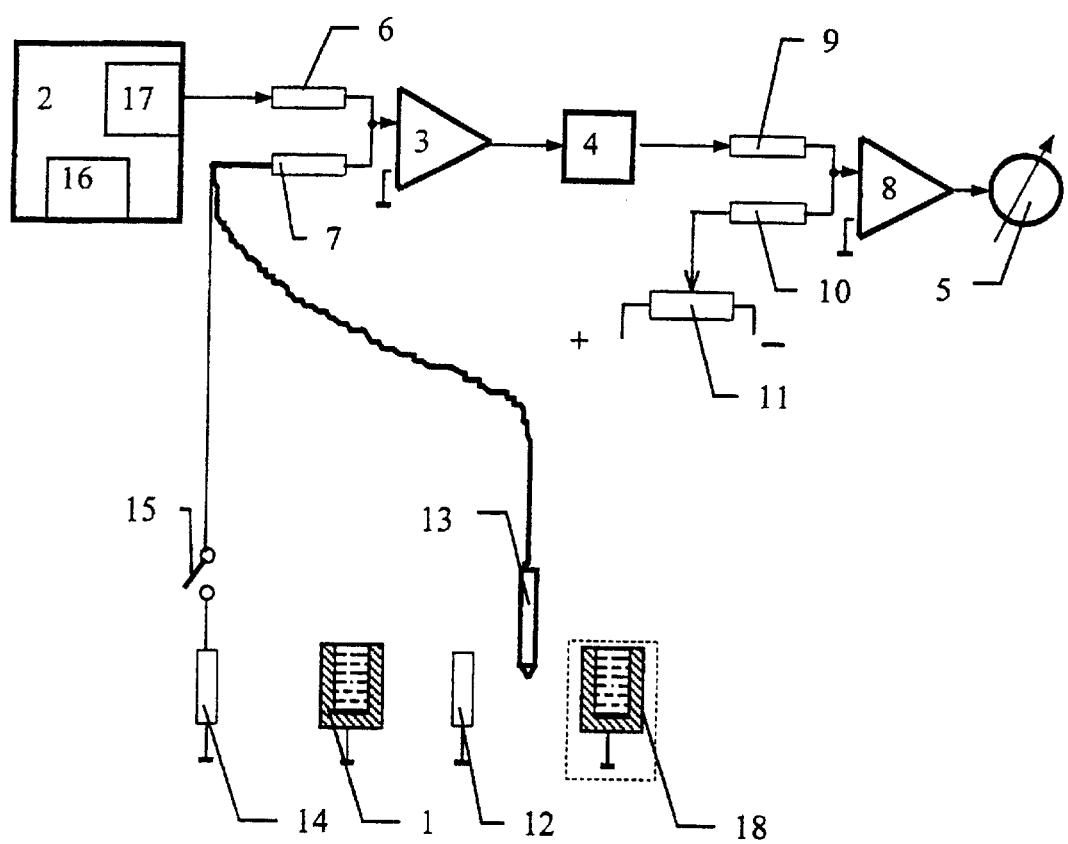
FIG. 1 is a functional block-diagram of the device.

The device for diagnosis of the physiological condition of a biological object (FIG. 1) comprises the analysis cell 1 intended for placing a biological fluid into it. The generator 2 is connected to the cell 1. The differential amplifier 3, the detector 4, the measuring unit 5 are connected in series. The cell 1 is made so as to allow its connection to the differential amplifier 3.

The differential amplifier 3 is made with the first and the second current summing inputs, 6 and 7, respectively. The generator 2 is connected to the first summing input 6 of the differential amplifier 3. The amplifier 8 is made with the first and the second summing inputs, 9 and 10, respectively. The device is provided with the voltage regulator 11 and the biological fluid reference 12. The electrode 13 is connected to the second summing input 7 of the differential amplifier 3 and made so as to allow its spatial displacement for making contact with a biological fluid in the analysis cell 1 and with the reference 12. The detector 4 is connected to the measuring unit 5 through the first summing input of the amplifier 8. The regulator 11 is connected to the measuring unit 5 through the second summing input of the amplifier 8.

As the reference 12 a biological fluid sample collected from a reference biological object (an earlier diagnosed healthy human being or animal) may be used, which is placed into the reference cell similar as to its electrical parameters to the analysis cell 1, after which the conductivity $Y_R$ of the biological fluid sample is measured in the reference cell. Or, as the reference 12 a resistor may be used that has a conductivity equal to that of the biological fluid in the reference cell containing a biological fluid. Also, as the reference 12, a set of resistors may be used for investigating various biological fluids, such as saliva, blood, urea.

The device may be supplemented with an equivalent of the electrode 13, which is made in the form of the resistor 14 having the conductivity equal to that of the electrode 13 and connected to the second summing input 7 of the differential amplifier 3 through a switch 15, which enables to allow for errors introduced directly by the electrode 13.

The generator 2 may be made capable of modulating the output signal frequency and amplitude, for which purpose it comprises a frequency regulator 16 and an attenuator 17 for amplitude modulation. The introduction of the frequency regulator 16 and the attenuator 17 enables to additionally improve the measurement accuracy due to conducting measurements in a resonance mode.

Figure 2:
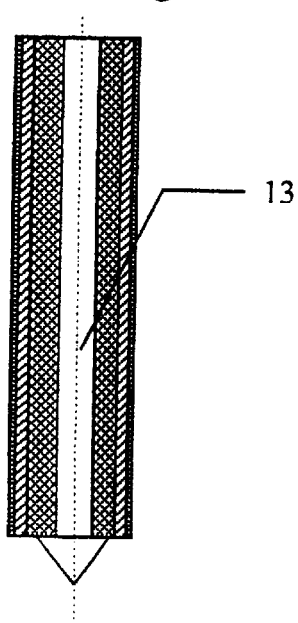
FIG. 2 shows the construction of the electrode made in the form of a probe.

To further improve the measurement accuracy, the electrode 13 (FIG. 2) may be made in the form of a coaxial probe with the cone-shaped tip, which enables to conduct measurements in a definite point, promptly clear it from biological fluids and exclude the effect of air bubbles in the near-electrode conical layer in the course of putting the probe into a biological fluid. Such a probe may be connected to the second input 7 of the differential amplifier 3 with a coaxial cable.

The making of the differential amplifier 3 with the first and the second current summing inputs 6 and 7 as well as the introduction of the amplifier 8 (all a differential one) with the first and the second current summing inputs 9 and 10 enables to preclude errors associated with potential measurements and constantly monitor the parameters of the electrode 13, and to compensate or eliminate measurement errors before measuring. The connection of the second summing input of the amplifier 8 with the regulator 11 enables to eliminate the effect of the signal direct component, extract and amplify the useful signal only, thus significantly expanding the range of measurements.

The device (FIG. 1) operates as follows.

First, a biological fluid sample is collected from a biological object (a human being or an animal), which is then placed in the analysis cell 1. A current supplied by the generator 2, which frequency and amplitude is modulated by the frequency regulator 16 and the attenuator 17, is passed through the cell 1. The conductivity Y1 is measured by the measuring unit 5. A biological fluid sample is collected from a biological object (a human being or an animal) just after his/its awakening, in the period when, as research show, the conductivity Y1 is the closest to the conductivity $Y_R$ of the reference 12, or slightly lower. A current of the same frequency and amplitude is passed through the reference 12 and its conductivity $Y_R$ is measured. The conductivity Y1 of the biological fluid in the cell 1 and that of the reference 12 by determining their ratio $N_1=Y1/Y_R$. If the value $N_1$ is less than 1, it evidences the normal condition of the biological object, but if it exceeds 1, it attests to a possible disease and a disorder of the physiological condition of the biological object. The further diagnosis of a disease is made by customary methods. The value of the electrical conductivity obtained in the first measurement is, as studies showed, in proportion to the maximum accumulation of alien components in the biological fluid.

For further express diagnosis the second biological fluid sample is collected from the biological object before the first meal (usually in 0.5–1 hour after awakening). The biological fluid is placed in the additional analysis cell 18 (FIG. 1) that is similar as to its electric parameters to the said cell 1. The conductivity Y2 of the second sample is measured. The conductivity Y2 of the biological fluid in the additional analysis cell 18 and the conductivity Y of the reference 12 by determining their ratio $N_2=Y2/Y_R$. The condition of the immune system of the biological object is determined by compliance with the value $1<N_1/N_2$; if the value of $N_2<1$, then the activity of the immune system grows (the normal condition of the biological object's immune system is diagnosed), but if the value of $N_2$ approaches to 1 from left or right ($0.95<N_2<2.1$), the activity of the immune system decreases (a possible disease of the immune system is diagnosed). The further diagnosis of a disease is made by customary methods. The value of the electrical conductivity obtained in the first measurement is, as studies showed, in proportion to the resistance of the biological object to external factors, and the relation between the first measurement and the second measurement upon expiration of the said time period characterizes the reaction of the biological object to the influence of external factors.

Since the measurements are conducted with the same probe in the similar ambient conditions (temperature, humidity, pressure, etc.) for the object under study, and the reference and the relation between the measured parameters is determined, random errors do not practically influence the studies and systematic errors are compensated owing to the proposed circuit design.

It is most advisable to use saliva as the biological fluid for express diagnosis, since it is the most descriptive and easy-to-collect biological fluid of a biological object, which is the easiest for studying by the proposed method. The specific resistance of the human saliva (without accounting for the resistance of the casing of the cell 1) for the reference 12 is 3.238 Ohm·m.

But, the method does not preclude the use of urea as a biological fluid (specific resistance is 2.08 Ohm·m) as well as blood (specific resistance is 1.62 Ohm·m).

When implementing the method, for the purpose of improving the accuracy, it is advisable to introduce an equivalent of the electrode 13, which is to be made in the form of a resistor 14 with the conductivity equal to that of the electrode 13. In such a case the electrode 13 is wiped dry and first left in the air, without introducing it into the cell 1. The regulator 11 is set in the neutral position. When the switch 15 is locked, the equivalent of the electrode 13, i.e., the resistor 14, is connected to the second summing input 7 of the differential amplifier 3. Upon summing, the resulting basic signal is fed to the measuring unit 5 from the generator 2 and through the first summing input of the differential amplifier 3, the detector 4 and the amplifier 8. The conductivity value $Yset_1$ is set at the measuring unit 5 with the regulator 11. The switch 15 is unlocked, and the electrode 13 is placed on the reference 12. When the conductivity value $Yset_2$, different from $Yset_1$, is obtained at the measuring unit 5, the measurement error, which is additionally introduced by the electrode 13, is evaluated by the difference between the two values. Thus, in the course of measuring conductivities of biological fluids it is always possible to take into account the time changes in the error introduced by the electrode 13 due, e.g., to oxidization of its contact surface.

In case the conductivity of a biological fluid is to be measured, the probe, i.e., the electrode 13, is brought into contact with the reference 12. For the purpose of making the measurement of the conductivity $Y_R$ stable the needed value of the output signal as to frequency and amplitude is selected with the frequency regulator 16 and the attenuator 17, thus setting the reference point. Then the sharp conical probe tip of the electrode 13 is brought into contact with the surface of the biological fluid in the analysis cell 1. The value proportional to the conductivity Y1 of the biological medium is recorded at the measuring unit 5. After this, as stated above, their relation is determined.

When measuring biological fluids, which are characterized by a low information signal and a high common signal, the attenuator 17 is set, in the course of adjusting it on the reference 12, in the position that corresponds to the maximum level of the output signal from the generator 2; and a new reference point is set with the voltage regulator 11 at the measuring unit 5 for measuring the conductivity of another biological fluid.

Example 1. Studied were blood, urea and saliva collected from patients with the grave condition of the respiratory system in the complication period. The values obtained were: $N_1=1.5-2.1$; $N_2=1.6-2.2$.

Example 2. A group of 27 sportsmen was studied. In the future 6 persons from the group were ill with influenza. The analyses conducted in accordance with the claimed method showed that for those 6 persons the value $N_1$ before the disease was in the range from 1.0 to 1.4, i.e., the activity of the immune system proved to be lowered, and in the future they had the said infection disease. For the rest members of the group the value $N_2$ was from 0.6 to 0.8, and the followed up persons had not got any diseases during the infectious period.

Example 3. The effects of external factors, such as high radiation background, excessive physical loads, over-eating, food-poisoning, troubled sleep, stress, etc, on the physiological condition of human beings were studied. For most negative factors stated above the values $N_1$ and $N_2$ were from 1.1 to 1.6; poisoning with nitrate-containing foodstuffs was characterized by values from 1.8 to 2.1.

Example 4. Various diseases of the urogenital system were studied. The value $N_2$ after surgery was 1.8 to 2.0; in a week after surgery—1.2–1.4.

Example 5. A group of 3 persons having the values $N_1$ and $N_2$ slightly exceeding 1 was followed up for 10 months. The studies showed that in a case where these values, especially $N_2$, are preserved at the level of 1.1–1.3 for more than 30 days, various diseases of the locomotor apparatus and the blood circulation system began to appear.

INDUSTRIAL APPLICABILITY

The claimed method of express diagnosis and device for realizing same may be most successfully used in medicine for integral assessment of the physiological condition of a human being or an animal.

What is claimed is:

1. A method of diagnosis of the physiological condition of a biological object, which involves collecting a biological fluid sample from a biological object, placing the sample in an analysis cell (1), passing an alternating current through the cell (1) for the analysis with a biological liquid, and measuring the biological fluid sample conductivity Y1 used for assessment of the physiological condition of the biological object, wherein the biological fluid sample is collected from the biological object after awakening, a reference (12) biological fluid is additionally used, an alternating current of the same frequency and amplitude is passed through the reference biological fluid (12) and its conductivity $Y_R$ is measured at constant temperatures of the reference and the analysis cell (1) containing the biological fluid, the conductivity values Y1 and $Y_R$ are compared by determining the ratio $N_1=Y1/Y_R$, where $N_1$ lower than 1 evidences the normal condition of the biological object and $N_1$ greater than 1 attests to a disorder in the physiological condition of the biological object.

2. The method according to claim 1, wherein the biological fluid sample collected from a reference biological object and used as the biological fluid reference (12) is placed in the reference cell is similar as to its electrical parameters to the analysis cell, and the conductivity $Y_R$ of the biological fluid sample contained in the reference cell is measured.

3. The method according to claim 1, wherein a resistor is used as the biological fluid reference (12), which has the conductivity equal to that of the biological fluid and the analysis cell.

4. The method according to claim 1, wherein a second biological fluid sample is collected from the biological object before a first meal and is placed in an additional analysis cell (18) similar as to its electrical parameters to the said analysis cell (1), the conductivity Y2 of the second sample is measured, the ratio $N_2=Y2/Y_R$ is determined by the biological fluid conductivity in the additional analysis cell (18) and that in the reference cell, and the condition of the immune system is assessed by the compliance with the relation $N_1/N_2>1$, where at the value $N_1<1$ the immune system activity grows, but if $N_1$ approaches to 1 it is reduced.

5. The method according to claim 1, wherein saliva is used as the biological fluid.

6. The method according to claim 1, wherein urea is used as the biological fluid.

7. The method according to claim 1, wherein blood is used as the biological fluid.

8. A device for diagnosis of the physiological condition of a biological object comprising an analysis cell (1) intended for placing a biological fluid therein, an alternating current generator (2) connected to the cell (1), and a differential amplifier (3), a detector (4), a measuring unit (5) that are connected in series, the cell (1) being made so as to allow its connection to the differential amplifier (3), wherein the differential amplifier (3) is made with first (6) and second (7) current summing inputs and providing summation on the mentioned current summing inputs (6), (7), the alternating current generator (2) is connected to the first summing input (6) of the differential amplifier;

further comprising an amplifier (8), which is made with first and the second summing inputs (9), (10) and providing summation on the mentioned inputs (9), (10), a voltage regulator (11), a biological fluid reference (12), an electrode (13) connected to the second summing input (7) of the differential amplifier (3) and made so as to allow spatial displacement of the electrode for making alternate contact with the analysis cell (1) for analysis or with the biological fluid reference (12), the detector (4) being connected to the measuring unit (5) through the first input (9) of the amplifier (8) and the voltage regulator (11) being connected thereto through the second input (10) of the amplifier (8).

9. The device according to claim 8, further comprising a correspondent to the electrode (13), which is made in the form of a resistor (14) having the conductivity equal to that of the electrode (13) and connected to the second input (7) of the differential amplifier (3) through a switch (15).

10. The device according to claim 8, wherein the generator (2) is made capable of modulating the output signal frequency and amplitude.

11. The device according to claim 8, wherein the electrode (13) is made in the form of a coaxial probe with the cone-shaped tip.

* * * * *